United States Patent
Altmann et al.

(10) Patent No.: US 11,504,042 B2
(45) Date of Patent: Nov. 22, 2022

(54) EXTENSION OF ELECTROCARDIOGRAPHY (ECG) ACQUISITION CAPABILITIES OF CATHETER-BASED CARDIAC SYSTEM

(71) Applicant: Biosense Webster (Israel) Ltd., Yokneam (IL)

(72) Inventors: Andres Altmann, Haifa (IL); Vadim Gliner, Haifa (IL); Alon Boumendil, Amiram (IL); Assaf Govari, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 211 days.

(21) Appl. No.: 16/817,545

(22) Filed: Mar. 12, 2020

(65) Prior Publication Data
US 2020/0397328 A1    Dec. 24, 2020

Related U.S. Application Data

(60) Provisional application No. 62/863,679, filed on Jun. 19, 2019.

(51) Int. Cl.
| | |
|---|---|
| *A61B 5/287* | (2021.01) |
| *A61B 5/282* | (2021.01) |
| *A61B 5/316* | (2021.01) |
| *A61B 5/00* | (2006.01) |

(52) U.S. Cl.
CPC .............. *A61B 5/287* (2021.01); *A61B 5/282* (2021.01); *A61B 5/316* (2021.01); *A61B 5/6858* (2013.01)

(58) Field of Classification Search
CPC ............................... A61B 5/287; A61B 5/282
USPC .................................................. 600/508–509
See application file for complete search history.

(56) References Cited

U.S. PATENT DOCUMENTS

| | | | |
|---|---|---|---|
| 9,398,862 B2 | 7/2016 | Harlev et al. | |
| 10,356,001 B1* | 7/2019 | Drakulic | ............... A61B 5/308 |
| 2007/0078354 A1 | 4/2007 | Holland | |
| 2012/0116387 A1* | 5/2012 | Govari | ............... A61B 18/1492 |
| | | | 606/41 |

FOREIGN PATENT DOCUMENTS

CN        109222941 A        1/2019

* cited by examiner

*Primary Examiner* — Nicole F Lavert
(74) *Attorney, Agent, or Firm* — Frost Brown Todd LLC

(57) ABSTRACT

A method includes receiving analog body-surface signal from body-surface electrode, and multiple analog unipolar signals from multiple unipolar electrodes of an invasive probe. A first unipolar electrode is assigned to serve as a common electrical ground and a common timing reference for the analog unipolar signals and the analog body-surface signal. The analog unipolar signals are digitized to produce digital unipolar signals sampled relative to a digital ground. Defined are an analog bipolar signal between the first unipolar electrode and a second unipolar electrode of the probe, and digital bipolar signal formed from the first unipolar electrode and the second unipolar electrode. Ground and timing offsets between the analog bipolar signal and the digital bipolar signal are estimated, while the first unipolar electrode is connected to the digital ground. The ground offset and the timing offset are applied in measuring a third unipolar signal, sensed by a third unipolar electrode.

20 Claims, 4 Drawing Sheets

EXTENSION OF ELECTROCARDIOGRAPHY (ECG) ACQUISITION CAPABILITIES OF CATHETER-BASED CARDIAC SYSTEM

CROSS-REFERENCE TO RELATED APPLICATIONS

This application claims the benefit of U.S. Provisional Patent Application 62/863,679, filed Jun. 19, 2019, whose disclosure is incorporated herein by reference.

FIELD OF THE INVENTION

The present invention relates generally to the acquisition and processing of electrophysiological signals, and particularly the processing of electrocardiogram (ECG) signals acquired using a catheter.

BACKGROUND OF THE INVENTION

Electrocardiography (ECG) is a well-established cardiac diagnostic technique. Various techniques were proposed in the patent literature for measuring ECG signals. For example, U.S. Pat. No. 9,398,862 describes, in some aspects, a method that includes measuring unipolar signals at one or more electrodes in response to electrical activity in a heart cavity. In some embodiments, signals are measured over several heart beats, either at a single catheter location within the heart chamber or over several locations. The method also includes determining, based at least in part on Laplace's equation, bipolar physiological information at multiple locations of a surface based on the measured unipolar signals and positions of the one or more electrodes with respect to the surface.

As another example, Chinese Patent Application Publication No. CN109222941A describes ECG pulse wave propagation time measurement methods and measuring apparatus. A synchronization acquisition method measures the pulse wave signal, extracts the pulse wave signal and an ECG feature point, and calculates the pulse transit time. According to ECG calculation of Presystolic period and using the calculated pulse transit time minus the Presystolic period, the method obtains pulse wave propagation time. The present invention removes the Presystolic period influence and improves the measurement accuracy of the pulse wave propagation times.

SUMMARY OF THE INVENTION

A method includes receiving (i) an analog body-surface signal from one or more body-surface electrodes attached externally to a patient, and (ii) multiple analog unipolar signals from multiple unipolar electrodes of a probe inserted in an organ of the patient. A first unipolar electrode is assigned, from among the multiple unipolar electrodes, to serve as a common electrical ground and a common timing reference for the analog unipolar signals and the analog body-surface signal. The analog unipolar signals are digitized to produce respective digital unipolar signals by sampling the analog unipolar signals relative to a digital ground. The following are defined: (i) an analog bipolar signal between the first unipolar electrode and a second unipolar electrode of the probe and (ii) a digital bipolar signal formed from respective digital unipolar signals derived from the first unipolar electrode and the second unipolar electrode. A ground offset and a timing offset between the analog bipolar signal and the digital bipolar signal are estimated, while the first unipolar electrode is connected to the digital ground.

The ground offset and the timing offset are applied in measuring a third unipolar signal, sensed by a third unipolar electrode of the catheter, relative to the body-surface signal.

In some embodiments, the analog unipolar signals and the digital unipolar signals include electrocardiograms.

In some embodiments, the analog body-surface signal includes a Wilson Central Terminal (WCT) signal.

There is additionally provided, in accordance with another embodiment of the present invention, an apparatus including circuitry and a processor. The circuitry is configured to: (a) receive an analog body-surface signal from one or more body-surface electrodes attached externally to a patient, (b) receive multiple analog unipolar signals from multiple unipolar electrodes of a probe inserted in an organ of the patient, (c) assign, from among the multiple unipolar electrodes, a first unipolar electrode to serve as a common electrical ground and a common timing reference for the analog unipolar signals and the analog body-surface signal, (d) digitize the analog unipolar signals to produce respective digital unipolar signals by sampling the analog unipolar signals relative to a digital ground, and (e) define (i) an analog bipolar signal between the first unipolar electrode and a second unipolar electrode of the probe and (ii) a digital bipolar signal formed from respective digital unipolar signals derived from the first unipolar electrode and the second unipolar electrode. The processor is configured to estimate a ground offset and a timing offset between the analog bipolar signal and the digital bipolar signal, while the first unipolar electrode is connected to the digital ground, and apply the ground offset and the timing offset in measuring a third unipolar signal, sensed by a third unipolar electrode of the probe, relative to the body-surface signal.

The present invention will be more fully understood from the following detailed description of the embodiments thereof, taken together with the drawings in which:

DETAILED DESCRIPTION OF EMBODIMENTS

Overview

Figure 1:
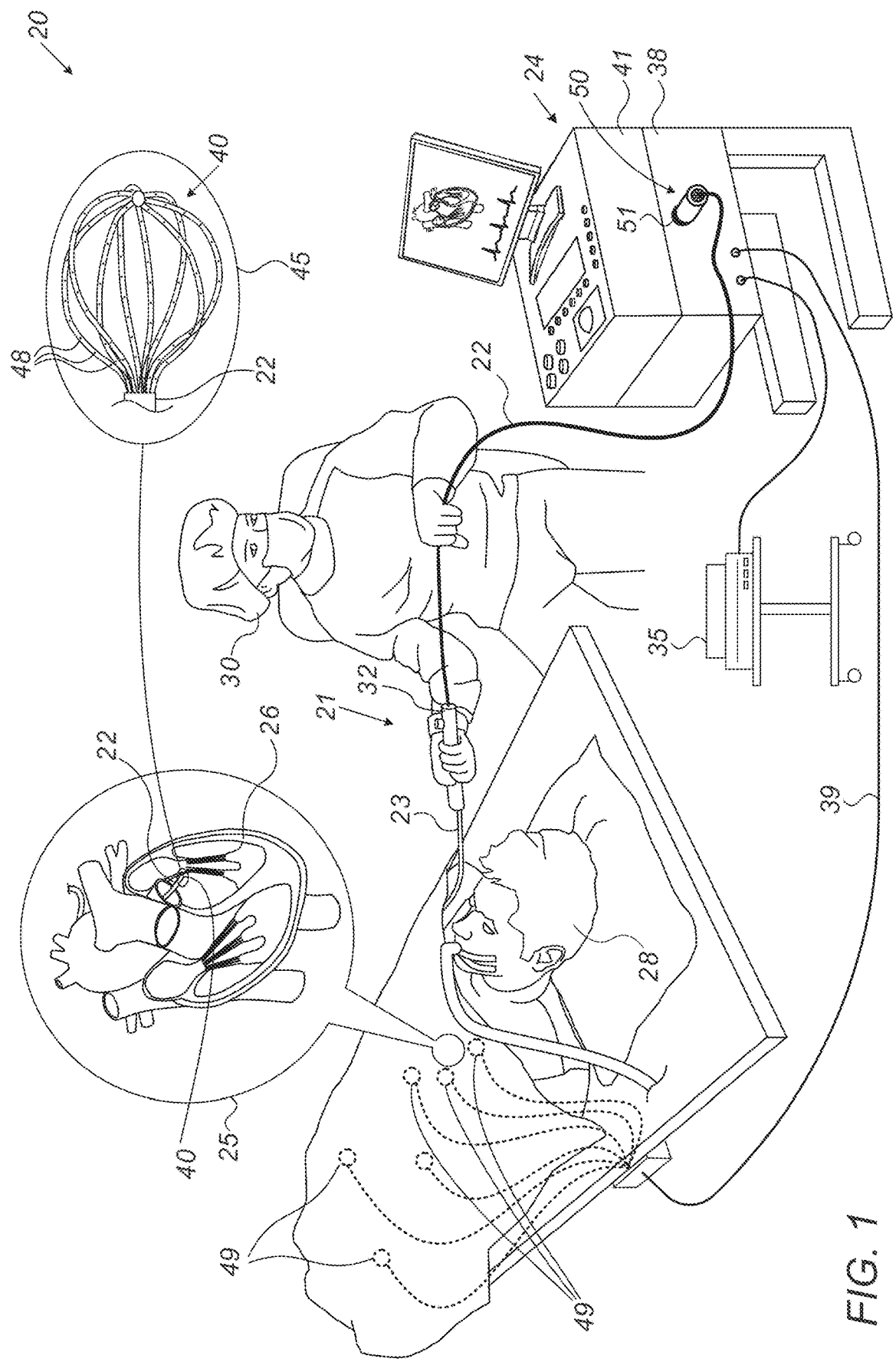
FIG. 1 is a schematic, pictorial illustration of a catheter-based electrophysiological sensing system, in accordance with an embodiment of the present invention.

Legacy catheter-based cardiac systems are sometimes configured to measure a limited number of signals, e.g., up to several tens of electrocardiogram (ECG) channels. Modern diagnostic catheters, however, may have many more electrodes, e.g., 256 electrodes that are inside an organ (e.g., heart) of the subject. To accommodate the extra channels of modern diagnostic catheters, signals from such a catheter (e.g., a 256-channel basket catheter) may be transmitted to a legacy catheter-based system via a digital communication link, to process all of the channels.

To have the analog signals from the catheter transmitted via the digital link, an analog to digital converter (ADC) module (referred to herein as an "ADC dongle" or simply "dongle") is inserted between the diagnostic catheter and the legacy catheter-based system.

Some clinical applications require acquiring the catheter signals as unipolar signals relative to a Wilson Central Terminal (WCT) ground coupled to a legacy system, which is formed from three body surface electrodes attached to the skin of a patient. WCT ground is obtained by averaging the three external active limb electrode voltages measured with respect to the return ground electrode, which is further described in "True Unipolar ECG Machine for Wilson Central Terminal Measurements" by Gaetano D. Gargiulo, The MARCS Institute, University of Western Sydney, Kingswood, NSW2747, Australia, May 2015, and "Wilson's Central Terminal, the keystone to electrogram recording—What, where and why?" published Apr. 23, 2013 by John Silberbauer, E P Fellow, San Raffaele Hospital, Milan, which are incorporated by reference in the Appendix.

Two problems arise when the legacy system processor comes to derive and analyze unipolar signals relative to a WCT ground using the digitized signals from any of the internally disposed catheter's 256 ECG channels.

The first problem is that the electrical ground of the ADC dongle, relative to which unipolar signals are digitized, and the ground of the legacy catheter-based system (e.g., WCT ground) are different. Therefore, the digitized unipolar amplitudes inputted from the catheter will have wrong amplitudes on the legacy catheter-based system.

The second problem is that the timing (e.g., signal phase) of the digitized signals and the timing of the WCT ground of the legacy catheter-based system are unrelated. The desynchronized signals (digitized catheter signals vs. analog ground signals) cannot thus be related one to the other (even if there were no issue of ground amplitude).

Embodiments of the present invention that are described hereinafter provide apparatuses and methods to overcome the lack of common ground and lack of signal synchronization described above between a legacy system and a modern diagnostic catheter coupled via a digital link. The disclosed techniques enable, for example, accurate measurement of multiple unipolar ECG signals using a legacy system.

In some embodiments, a disclosed apparatus is provided in order to overcome the lack of common ground and lack of signal synchronization described above. The apparatus comprises interface circuitry of the legacy system, which is configured to receive an analog body-surface signal from one or more body-surface electrodes attached externally to the patient (e.g., a WCT ground signal).

The disclosed apparatus further comprises an additional (e.g., an add-on or a stand-alone) circuitry comprising an ADC module, wherein the additional circuitry is configured to receive multiple analog unipolar signals from multiple unipolar electrodes of a probe inserted in an organ of the patient, assign, from among the multiple unipolar electrodes, a first unipolar electrode to serve as a common electrical ground and a common timing reference for the analog unipolar signals and the analog body-surface signal, digitize the analog unipolar signals to produce respective digital unipolar signals by sampling the analog unipolar signals relative to a digital ground, and define (i) an analog bipolar signal between the first unipolar electrode and a second unipolar electrode of the probe and (ii) a digital bipolar signal formed from respective digital unipolar signals derived from the first unipolar electrode and the second unipolar electrode.

The disclosed apparatus further comprises a processor of the legacy system that is configured to estimate a ground offset and a timing offset between the analog bipolar signal and the digital bipolar signal, while the first unipolar electrode is connected to the digital ground, and apply the ground offset and the timing offset in measuring a third unipolar signal, sensed by a third unipolar electrode of the probe (e.g., catheter), relative to the body-surface signal.

In other words, the disclosed technique sacrifices one of the electrodes of the probe, and uses this electrode to serve as a common ground and a common timing reference between the digitized signals and for the original analog signals.

To estimate the timing offset, the processor of the legacy system commands the interface circuitry to apply high-pass filtering (i.e., "skews") to both the analog bipolar signal input and the digital bipolar signals. The two bipolar signals are then routed into a cross-correlator circuit of the legacy system that cross-correlates the two bipolar signals. In an embodiment, using the cross-correlated bipolar signals, the processor synchronizes the clocks of the legacy system and the dongle signals to cancel the timing offset between the analog and digital bipolar signals.

To apply the ground offset in measuring the third unipolar signal, after the timing offset was applied, the processor of the legacy system calculate a respective unipolar signal acquired by the third electrode of the probe. The processor can calculate the unipolar voltage by calculating from any third catheter electrode X, the value of $V_x - V_{WCT}$ X=1, 2, . . . , 256, i.e., for a digitized signal from any catheter electrode which is transmitted via the digital link, as described below.

Typically, the processor is programmed in software containing a particular algorithm that enables the processor to conduct each of the processor related steps and functions outlined above.

The disclosed technique provides a simple and effective means to enable the legacy system to accurately measure multiple unipolar signals acquired by multiple electrodes of a modern catheter. Thus, the disclosed technique may increase the availability of modern catheter-based diagnostic services.

System Description

FIG. 1 is a schematic, pictorial illustration of a catheter-based electrophysiological sensing system 20, in accordance with an embodiment of the present invention. System 20 may be, for example, a CARTO® 3 system, produced by Biosense-Webster, Irvine, Calif. As seen, system 20 comprises a catheter 21, having a shaft 22 that is navigated by a physician 30 into a heart 26 of a patient 28. In the pictured example, physician 30 inserts shaft 22 through a sheath 23, while manipulating shaft 22 using a manipulator 32 near the proximal end of the catheter.

In the embodiment described herein, catheter 21 may be used for any suitable diagnostic purpose, such as electrophysiological mapping of heart 26. An ECG recording instrument 35 may receive various types of ECG signals sensed by system 20 during the process.

As shown in inset 25, a distal end of shaft 22 of catheter 21 is fitted with a multi-electrode basket catheter 40. Inset 45 shows an arrangement of multiple sensing-electrodes 48 (i.e., 256 or more channels) of basket catheter 40. The proximal end of catheter 21 is connected by ADC dongle 50 to a control console 24. ADC dongle 50 accommodates extra channels from multiple electrodes 48 by digitizing all the catheter channels and transmitting the digitized signals to a digital link 51 of control console 24.

Console 24 comprises a processor 41, typically a general-purpose computer, with suitable front end and interface circuits 38 for receiving ECG signals as well as non-ECG signals (such as position signals) from sensing-electrodes 48 of catheter 21. Electrodes 48 may include 256 or more sensing n electrodes and each electrode of electrode 48 will be referenced as "electrode 48 #1, #2, #3 . . . #n" disposed inside or near the heart. For this purpose, processor 41 is connected to sensing electrodes 48 via wires running within shaft 22. Interface circuits 38 are further configured to receive ECG signals as well as non-ECG signals from surface body electrodes 49. Typically, electrodes 49 are attached to the skin around the chest and legs of patient 28. Processor 41 is connected to electrodes 49 by wires running through a cable 39 to receive signals from electrodes 49.

Four of surface body electrodes 49 are named according to standard ECG protocols: MA (right arm), LA (left arm), ML (right leg), and LL (left leg). A Wilson Central Terminal (WCT) may be formed by three of the four named body surface electrodes 49, and a resulting ECG signal, $V_{WCT}$, is received by interface circuits 38.

To overcome the above described lack of synchronization between signals acquired by catheter electrodes 48 and surface body electrodes 49, system 20 has two of the catheter electrodes connected also to interface circuits 38 via a first split cable 52. In this way the legacy system directly receives the analog bipolar signal. In addition, the two aforementioned catheter electrodes provide the digital bipolar signal relative to a digital ground formed by a second split cable 54 electrically grounding one of the electrodes to a ground of dongle 50. Wirings 52 and 54 enable processor 41 of legacy system 20 to synchronize the two bipolar signals, and subsequently to accurately derive and present catheter unipolar ECG signals from electrodes 48 on legacy system 20, as described below.

Processor 41 is typically programmed in software to carry out the functions described herein. The software may be downloaded to the processor in electronic form, over a network, for example, or it may, alternatively or additionally, be provided and/or stored on non-transitory tangible media, such as magnetic, optical, or electronic memory. In particular, processor 41 runs a dedicated algorithm as disclosed herein, included in FIG. 3, that enables processor 41 to perform the disclosed steps, as further described below.

Extension of ECG Acquisition Capabilities of Catheter-Based Cardiac System

Figure 2A:
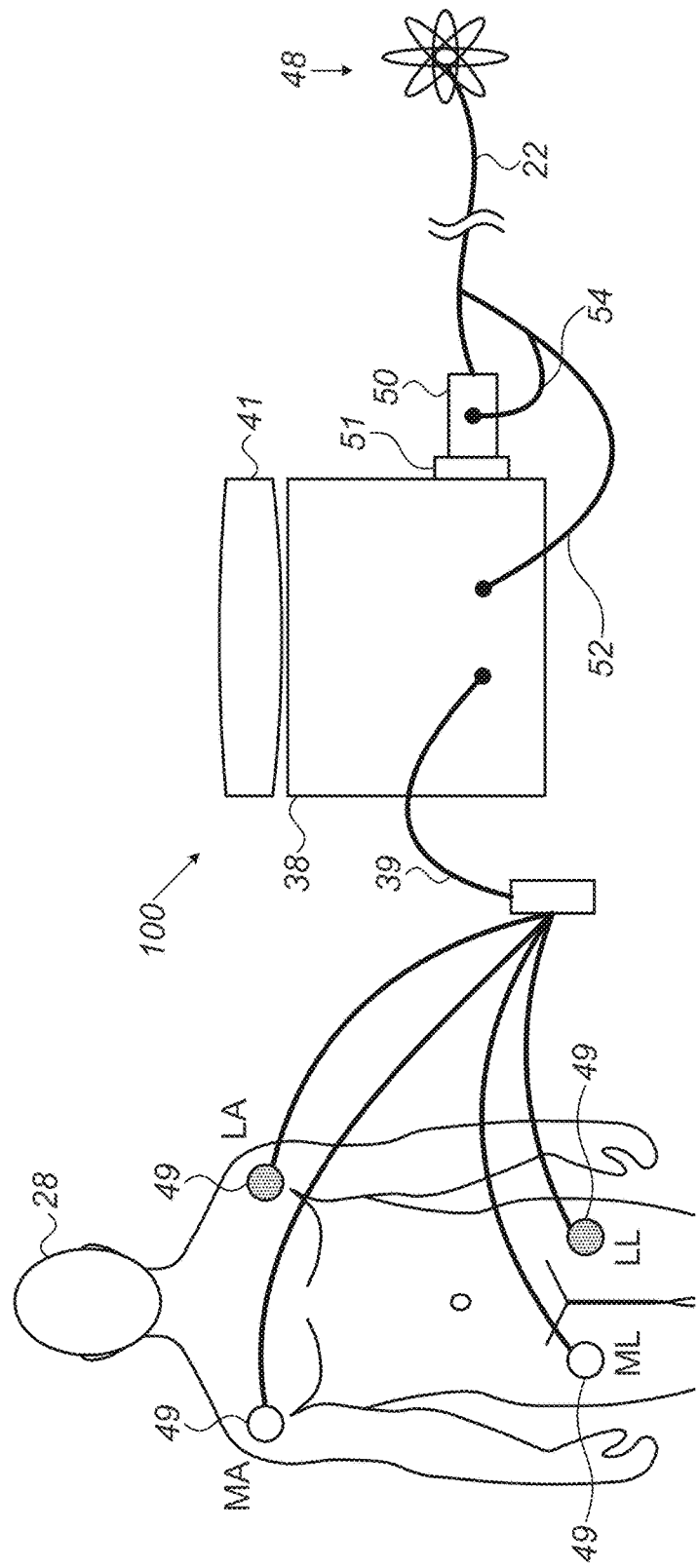
FIGS. 2A-2C are pictorial illustrations and an electrical diagram of an apparatus that enables the system of FIG. 1 to measure unipolar signals from a catheter, in accordance with an embodiment of the present invention.
Figure 2B:
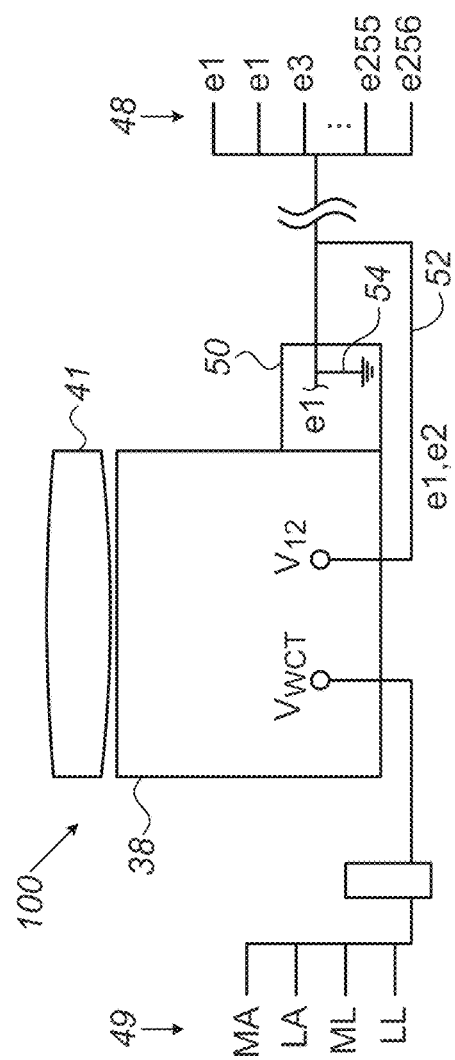
Figure 2C:
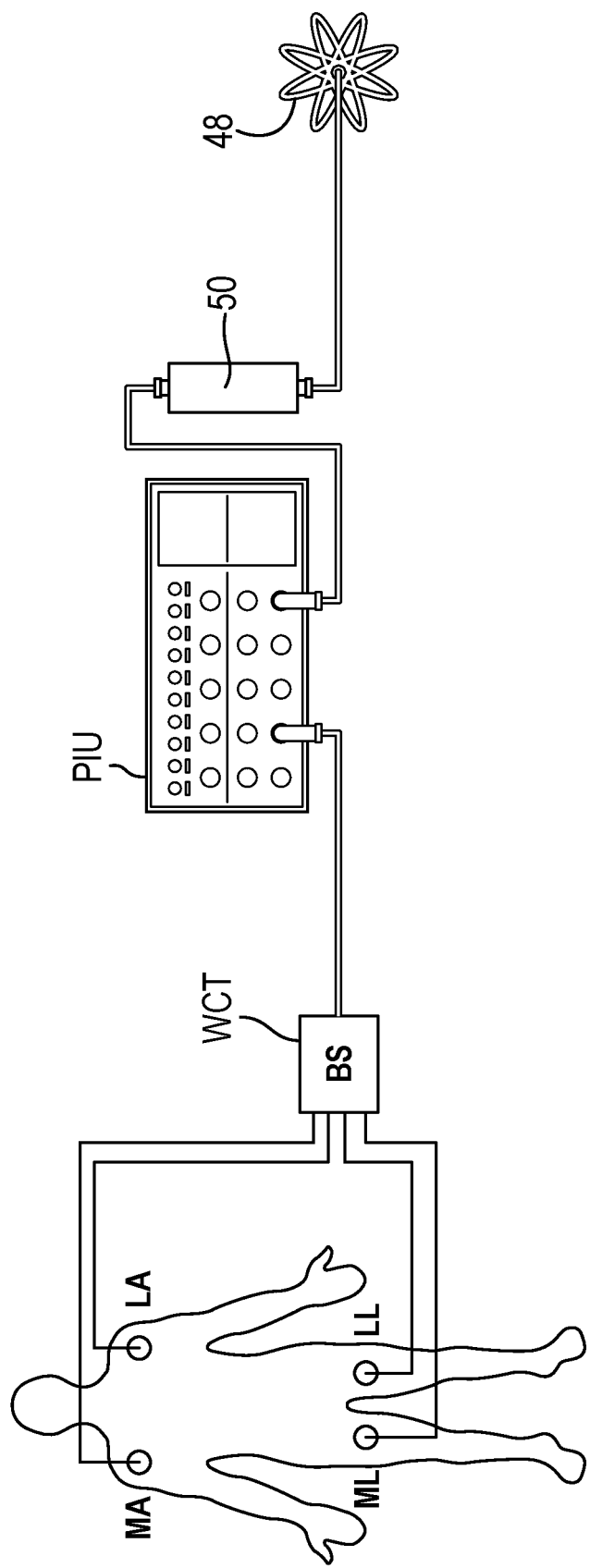

FIGS. 2A-2C are pictorial illustrations and an electrical diagram of an apparatus 100 that enables the system of FIG. 1 measuring unipolar signals from catheter 21, in accordance with an embodiment of the present invention.

As seen in FIG. 2A, interface circuits 38 receive electrical signals from surface body electrodes 49 via cable 39. Electrodes 49 are typically attached to the patient skin around the chest and legs of patient 28. Four of electrodes 49 are shown: MA (right arm), LA (left arm), ML (right leg), LL (left leg). A Wilson Central Terminal (WCT) is formed by three of the four shown body surface electrodes 49, and a resulting ECG signal, $V_{WCT}$, is received by interface circuits 38, as shown in FIG. 2B.

As further seen in FIG. 2B, electrodes 48 #1 and #2 are wired by cable 52 into an input socket of interface circuits 38, which directly receives, in this way, an analog bipolar signal $V_{12}$. Note that any other two electrodes 48 of the 256 or more electrodes of catheter 21 may be used, and there is no loss of generality in using electrodes #1 and #2. All 256 or more of electrodes 48, also including electrodes #1 and #2, are connected to interface circuits 38 via dongle 50 that is plugged into a socket of digital link 51. As seen, electrode #1 is grounded inside dongle 50 via cable 54 to a ground of ADC dongle 50.

Processor 41 receives, via ADC dongle 50 via digital link 51 in interface circuits 38, an input set of signals comprising the set of measured and digitized bipolar signals, $(V_x-V_1)$, X=2, . . . , n where n is 256 or more. Processor 41 further directly receives, via interface circuits 38, a measured ground offset signal $(V_1-V_{WCT})$ that the processor can now add to the synchronized digitized signals bipolar signals, $(V_x-V_1)$ to derive unipolar signals. Processor 41 derives each of the remaining 255 unipolar signals $V_x-V_{WCT}$, (i.e., relative to $V_{WCT}$) by calculating the following additive calculation:

$$V_x - V_{WCT} = (V_x - V_1) + (V_1 - V_{WCT}), X=2, \ldots, n \qquad \text{Eq. 1}$$

As shown in FIG. 2C, the schematic arrangement shown in FIG. 2A (for the CARTO® 3 system of FIG. 1) can be implemented with body surface sensors "BS" connected to the patient-interface-unit (PIU). The PIU is also connected to dongle 50 with the diagnostic catheter 48. In this prototype, both the circuit 38 and processor 41 are combined into the PIU.

Figure 3:
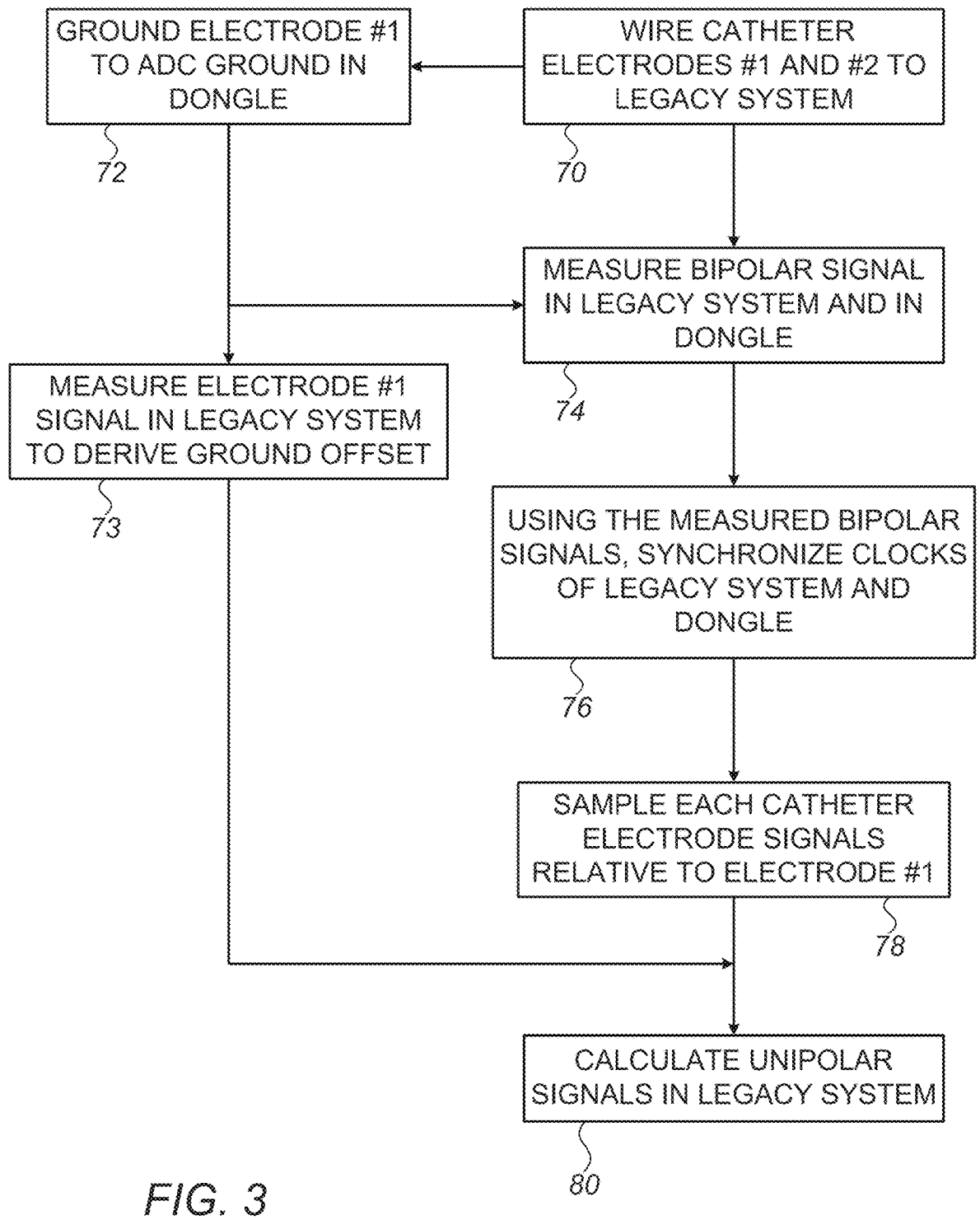
FIG. 3 is a flow chart that schematically illustrates a method for measuring multiple unipolar signals from a catheter using the system of FIG. 1, in accordance with an embodiment of the present invention.

FIG. 3 is a flow chart that schematically illustrates a method for measuring multiple unipolar signals from a catheter using the system of FIG. 1, in accordance with an embodiment of the present invention. The algorithm according to the present embodiment carries out a process that begins with wiring catheter 21 electrode 48 #1 (i.e., the first electrode) and 48 electrode 48 #2 (e.g., from among the 256 electrodes of catheter 21) directly to interface circuits 38 of system 20 before signals from the two are digitized, at a first wiring step 70. At a second wiring step 72, electrode 48 #1 is grounded to a ground of ADC dongle 50.

At a ground offset extraction step 73, the analog potential of electrode 48 #1 is measured by interface circuits 38 and compared with the WCT potential to derive ground offset $V_1 - V_{WCT}$.

In parallel, interface circuits 38 measure an analog bipolar signal and a digital bipolar signal that was digitalized from same source of the analog bipolar signal, at bipolar signals measurement step 76.

Using the measured analog and digital bipolar signals, interface circuits 38 synchronizes the clocks of system 20 and ADC dongle 50, at a clock synchronization step 76.

At a sampling step 78, catheter signals from each electrode are digitally sampled relative to electrode 48 #1, by ADC dongle 50.

Finally, at a unipolar signal calculation step 80, for a third digitized signal from any electrode 48 different than electrodes 48 #1 and #2, processor 41 calculates, using Eq. 1, a respective unipolar signal relative to the WCT ground.

The example configurations shown in the figures are chosen purely for the sake of conceptual clarity. In alternative embodiments, the disclosed techniques may use other suitable configurations comprising other wiring schemes, different standalone interfaces, and other types of catheters than a basket catheter.

It will be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A method, comprising:
receiving, at a circuit, (i) an analog body-surface signal created from one or more body-surface electrodes attached externally to a patient, and (ii) a plurality of analog unipolar signals created from a plurality of unipolar electrodes inserted in the patient;
assigning, by the circuit, from among the plurality of unipolar electrodes, a first unipolar electrode and a second unipolar electrode, the first unipolar electrode being configured to serve as a common electrical ground and a common timing reference for the plurality of analog unipolar signals and the analog body-surface signal;
digitizing, by the circuit, the plurality of analog unipolar signals to produce a plurality of respective digital unipolar signals by sampling the plurality of analog unipolar signals relative to the common electrical ground;
defining, using a processor, (i) an analog bipolar signal based on the analog unipolar signals of the first unipolar electrode and the second unipolar electrode and (ii) a digital bipolar signal formed from the plurality of respective digital unipolar signals
estimating, using the processor, a ground offset and a timing offset between the analog bipolar signal and the digital bipolar signal, while the first unipolar electrode is connected to the common electrical ground; and
applying, using the processor, the ground offset and the timing offset in measuring a third unipolar signal, sensed by a third unipolar electrode of the plurality of unipolar electrodes, relative to the analog body-surface signal.

2. The method according to claim 1, the plurality of analog unipolar signals and the plurality of respective digital unipolar signals comprising electrocardiograms.

3. The method according to claim 1, the circuit comprising a Wilson Central Terminal (WCT) signal.

4. The method according to claim 3, the analog body-surface signal being received by the WCT.

5. The method according to claim 1, the circuit comprising an analog to digital converter (ADC) module.

6. The method according to claim 5, the plurality of analog unipolar signals being received by the ADC.

7. The method according to claim 6, the plurality of analog unipolar signals being digitized by the ADC.

8. The method according to claim 1, further comprising passing, using the processor, the analog bipolar signal and the digital bipolar signal through a high-pass filter.

9. The method according to claim 1, further comprising passing, using the processor, the analog bipolar signal and the digital bipolar signal through a cross-correlator circuit.

10. An apparatus, comprising:
circuitry, which is configured to:
receive an analog body-surface signal created from one or more body-surface electrodes configured to externally attach to a patient;
receive a plurality of analog unipolar signals created from a plurality of unipolar electrodes configured to be inserted in the patient;
assign, from among the plurality of unipolar electrodes, a first unipolar electrode and a second unipolar electrode, the first unipolar electrode being configured to serve as a common electrical ground and a common timing reference for the plurality of analog unipolar signals and the analog body-surface signal; and
digitize the plurality of analog unipolar signals to produce a plurality of respective digital unipolar signals by sampling the plurality of analog unipolar signals relative to the common electrical ground;
a processor, which is configured to:
define (i) an analog bipolar signal based on the analog unipolar signals of the first unipolar electrode and the second unipolar electrode and (ii) a digital bipolar signal formed from the plurality of respective digital unipolar signals;
estimate a ground offset and a timing offset between the analog bipolar signal and the digital bipolar signal, while the first unipolar electrode is connected to the common electrical ground; and
apply the ground offset and the timing offset in measuring a third unipolar signal, sensed by a third unipolar electrode of the plurality of unipolar electrodes, relative to the analog body-surface signal.

11. The apparatus according to claim 10, the processor and a portion of the circuitry being included in a legacy system.

12. The apparatus according to claim 10, the plurality of analog unipolar signals and the plurality of respective digital unipolar signals comprising electrocardiograms.

13. The apparatus according to claim 10, the circuitry comprising a Wilson Central Terminal (WCT).

14. The apparatus according to claim 13, the analog body-surface signal being received by the WCT.

15. The apparatus according to claim 10, the circuitry comprising an analog to digital converter (ADC) module.

16. The apparatus according to claim 14, the plurality of analog unipolar signals being received by the ADC.

17. The apparatus according to claim 15, the plurality of analog unipolar signals being digitized by the ADC.

18. The apparatus according to claim 10, the processor being further configured to the analog bipolar signal and the digital bipolar signal through a high-pass filter.

19. The apparatus according to claim 10, the processor being further configured to pass the analog bipolar signal and the digital bipolar signal through a cross-correlator circuit.

20. A system, comprising:
an analog to digital converter (ADC) configured to:
receive a plurality of analog unipolar signals created from a plurality of unipolar electrodes configured to be inserted in a patient, a first electrode from the unipolar electrodes being connected to ground within the ADC; and generate a plurality of respective digital unipolar signals based on the plurality of analog unipolar signals and the first electrode, and a processing device configured to receive (i) an analog body-surface signal created from one or more body-surface electrodes configured to externally attach to the patient, (ii) two analog unipolar signals associated with the first electrode and a second electrode, and (iii) the plurality of respective digital unipolar signals;

the processing device comprising a computer readable storage medium having computer readable program code embodied therewith and executable by at least one processor to:

generate, based on the two analog unipolar signals, an analog bipolar signal;

generate, based on the plurality of respective digital unipolar signals, a digital bipolar signal;

determine a ground offset factor and a timing offset factor between the analog bipolar signal and the digital bipolar signal; and apply the ground offset factor and the timing offset factor at least one signal within the plurality of respective digital unipolar signals.

\* \* \* \* \*